United States Patent [19]
Prevost et al.

[11] Patent Number: 5,772,964
[45] Date of Patent: Jun. 30, 1998

[54] NOZZLE ARRANGEMENT FOR COLLECTING COMPONENTS FROM A FLUID FOR ANALYSIS

[75] Inventors: Thomas H. Prevost, Bergen, N.Y.; James L. Dwyer, Concord, Mass.

[73] Assignee: Lab Connections, Inc., Marlborough, Mass.

[21] Appl. No.: 599,020

[22] Filed: Feb. 8, 1996

[51] Int. Cl.$^6$ .................................................. G01N 30/02
[52] U.S. Cl. .......................... 422/70; 422/89; 210/198.2; 210/656; 436/174; 436/164
[58] Field of Search ................................. 422/64, 70, 89; 436/164, 43, 154, 171, 174; 356/36; 210/198.2, 656; 250/288 A

[56] References Cited

U.S. PATENT DOCUMENTS

| | | | |
|---|---|---|---|
| 4,080,833 | 3/1978 | Huber | 73/423 A |
| 4,604,362 | 8/1986 | Park et al. | 436/34 |
| 4,820,044 | 4/1989 | Crighton et al. | 356/315 |
| 4,823,009 | 4/1989 | Biemann et al. | 250/341 |
| 4,883,958 | 11/1989 | Vestal | 250/288 |
| 5,039,614 | 8/1991 | Dekmezian et al. | 436/43 |
| 5,238,653 | 8/1993 | Bourne | 422/70 |
| 5,268,103 | 12/1993 | Jameson et al. | 210/634 |
| 5,384,024 | 1/1995 | Moring et al. | 204/299 R |

OTHER PUBLICATIONS

Gagel et al., "Continuous Infrared Spectroscopic Analysis of Isocratic and Gradient Elution Reversed–Phase Liquid Chromatography", Analytical Chemistry vol. 59, No. 9, pp. 1266–1272, May 1, 1987.
Prior Invention of Claims 1–5.
"Instruction Manual LC–Transform System Series 100," Lab Connections, Inc., Marlborough, MA (Dec. 1994).

Gagel, "Continuous Recording of Fourier Transform Infrared Spectra of Compounds Eluted from a Liquid Chromatograph," Feb. 1988.

"The Linear Capillary Nozzle—A Quantum Advance in Sensitivity," Lab Connections, Inc., Marlborough, MA Mar., 1996.

Lange et al., "Reversed–Phase Liquid Chromatography/Fourier Transform Infrared Spectrometry Using Concentric Flow Nebulization", Apr. 15, 1991, *Analytical Chemistry* vol. 63, No. 8, pp. 782–787.

Gagel et al., "Continuous Recording of Reflection–Absorbance Fourier Transform Infrared Spectra of the Effluent of a Microbore Liquid Chromatograph", Sep. 1986, *Analytical Chemistry* vol. 58, No. 11, pp. 2185–2189.

Vestal et al., "Automatic Thermospray Controller for Gradient Elution Liquid Chromatography/Mass Spectroscopy", 1986, *International Journal of Mass Spectroscopy and Ion Processes*, vol. 70, pp. 185–194.

*Primary Examiner*—Harold Y. Pyon
*Attorney, Agent, or Firm*—Fish & Richardson P.C.

[57] ABSTRACT

A system for processing fluid carrying a component by depositing the component onto a medium and evaporating the fluid. The system includes a collection medium and a nozzle arrangement. The nozzle arrangement includes a long capillary with a first, inlet end for receiving a flow of the fluid carrying the component and a second, outlet end arranged near the collection medium. A heater is provided for heating the capillary. A sheath gas is directed toward the collection medium in a manner that the fluid is exposed to the sheath gas after emerging from the outlet end of the capillary. The long capillary may be bent, e.g., in a helical configuration, so that, in spite of its length, a nozzle of practical size for an analytical instrument can be provided.

17 Claims, 5 Drawing Sheets

NOZZLE ARRANGEMENT FOR COLLECTING COMPONENTS FROM A FLUID FOR ANALYSIS

FIELD OF THE INVENTION

This invention relates to collecting components from a fluid for analysis.

BACKGROUND OF THE INVENTION

In chromatography, chemical components in a mixture are separated by injecting the mixture onto a medium and flowing a solvent along the medium. The components in the mixture elute sequentially in an order dependent upon their relative affinity for the medium and the solvent.

It is useful in many fields to characterize and identify the separated components using spectroscopic techniques, such as infrared spectroscopy and mass spectrometry. However, these analyses are complicated by the presence of the chromatographic solvent. For example, most solvents are highly infrared absorbing and thus give rise to bands that obscure the infrared spectrum of the components. Analysis by mass spectrometry is complicated by evaporation of the solvent which interferes with the high vacuum environment required for operation of the spectrometer.

Accordingly, systems have been developed that evaporate the solvent while depositing the components onto a surface suitable for later use with a spectrometer. One such technique employs a nozzle assembly that includes an inner tubular element, through which the effluent flows, and an outer tubular element arranged concentric to the inner tubular element, through which a heated gas flows. The effluent is heated along the length of the inner tube and, upon emerging, is entrained in the gas flow to effect evaporation of the solvent and spray the component onto a collection surface. The collection surface is slowly traversed under the spray from the nozzle such that the components are deposited sequentially along a path.

The sensitivity of these systems is primarily dependent upon the ability of the nozzle to deposit the component in a small area while evaporating the solvent. For a given quantity of deposited component, spectroscopic sensitivity is approximately proportional to the inverse of the square of the deposit diameter. The operating parameters of the system, such as the type of chromatographic fluid and the fluid flow rate, and the nozzle gas flow rate and temperature are carefully controlled to deposit the components on the surface in the smallest achievable dimensions. But concentrating the nozzle spray into a smaller region makes it more difficult to evaporate the solvent. The experiment is also more difficult when using higher flow rates and less volatile solvents, such as aqueous solvents, which are common in chromatography. Reducing the diameter of the inner tube will reduce the dimensions of the spray cone, but it will also reduce the evaporative capacity.

SUMMARY OF THE INVENTION

An object of this invention is to provide a nozzle with high evaporative capacity that can produce small component deposits. The invention relates to a system including a nozzle with a capillary which is of substantial length to easily and consistently effect deposition in a narrow region from relatively high flow rates of chromatographic solvents of low volatility. The capillary can be arranged in a bent pattern, such as a helical pattern, so that in spite of its extended length, a system of convenient, practical dimensions for an analytical instrument can be constructed.

Without being limited to a theory, it is believed that the use of a long capillary, as described herein, creates very gradual countervailing temperature and pressure gradients which permit the fluid to be heated in a very gradual, controlled manner such that it is evaporated rapidly upon emerging from the nozzle and deposits the component in a small area. In particular, the capillary, because of its small diameter and its extended length, creates a large fluid back pressure at its inlet and a very gradual pressure gradient down its length to ambient pressure at the capillary tip outlet. The temperature of the fluid rises gradually along the length of the capillary from inlet to outlet. Since the vaporization temperature of a fluid increases with pressure, the fluid within the capillary can attain temperatures above its atmospheric boiling point without evaporating. This means that more heat can be applied to the fluid without premature vaporization.

Importantly, the pressure is not released rapidly, which can result in an erratic spray, causing nonuniform or large-area component deposits, or premature evaporation, causing nozzle plugging. Rather, the pressure is released gradually over the extended length of the capillary, which permits careful control of the spray pattern to effect small area deposits. Vaporization takes place in the zone immediately adjacent to the capillary tip. These factors result in small pattern deposition performance from the nozzle at significantly enhanced liquid flow rates. For example, as illustrated in experiments described below, the long capillary nozzles are capable of depositing components on a surface at atmospheric pressure in an area of about 500 $\mu$m width, at flow rates of about 150 $\mu$l/min using aqueous solvents.

In one aspect, the invention features a system for processing fluid carrying a component by depositing the component onto a medium and evaporating the fluid. The system includes a collection medium and a nozzle arrangement. The nozzle arrangement has a capillary with first, inlet end for receiving a flow of the fluid carrying the component and a second, outlet end arranged near the collection medium. A heater is provided for heating a substantial region of the capillary. A sheath gas is directed toward the collection medium in a manner that the fluid is exposed to the sheath gas after emerging from the outlet end of the capillary. The capillary has a length of about 10 cm or more.

In another aspect, the invention features a system for processing a fluid carrying a component by depositing the component onto a surface and evaporating the fluid. The system includes a collection medium and a nozzle arrangement. The nozzle arrangement includes a capillary with a first, inlet end for receiving a flow of the fluid carrying the component and a second, outlet end arranged near the collection surface. The nozzle arrangement also includes a heater for heating a substantial region of the capillary and a sheath gas directed toward the collection surface in a manner that the fluid is exposed to the sheath gas after emerging from the outlet end of the capillary. The capillary has a length and is arranged in a bent configuration such that the inlet end and outlet end are positioned at a distance less than the length.

In another aspect, the invention features a system for processing chromatographic effluent fluid carrying a component to facilitate spectroscopic analysis of the component by depositing the component onto a medium and evaporating the fluid. The system includes a collection medium compatible with the fluid and suitable for use in spectroscopic analysis and a nozzle arrangement. The nozzle arrangement includes a capillary with a first, inlet end for receiving a flow of the fluid and a second, outlet end arranged near the collection medium. The capillary has a length of about 20 to 30 cm and an inner diameter of about 75 to 150 µm. The capillary is arranged in a bent configuration such that the inlet end and the outlet end of the capillary are positioned at a distance that is less than the length. The nozzle arrangement includes a chamber for substantially containing the capillary. The chamber is arranged to receive a sheath gas and to direct the sheath gas toward the collection medium such that the fluid is exposed to the sheath gas after emerging from the outlet end of the capillary. The nozzle arrangement also includes a heater for heating the capillary over a substantial region upstream of the outlet end.

In another aspect, the invention features a method of processing fluid carrying a component to facilitate spectroscopic analysis of the component by depositing the component on a medium and evaporating the solvent. The method includes providing a collection medium compatible with the fluid and suitable for use in spectroscopic analysis and providing a nozzle arrangement. The nozzle arrangement includes a capillary with a first, inlet end for receiving a flow of the fluid and a second, outlet end arranged near the collection medium. The capillary has a length of about 20 to 30 cm and an inner diameter of about 75 to 200 µm. The arrangement also includes a heater for heating the capillary over a substantial region upstream of the outlet end. The method includes depositing the component onto the collection medium while evaporating the fluid under atmospheric conditions, transferring the collection medium to a spectrometer, and analyzing the component by spectrometry.

Embodiments may include one or more of the following features. The capillary has a length of about 15 to 50 cm, such as about 20 to 30 cm. The capillary has an inner diameter of about 75 to 200 µm, such as about 100 µm. The capillary is bent in helical fashion. The distance between the inlet end and the outlet end is about 5 cm or less. The capillary is substantially contained in a chamber having dimensions less than the length of the capillary. The chamber is arranged to receive the sheath gas and direct the sheath gas toward the collection medium. The chamber includes a heater. The heater is arranged to heat the chamber. The system includes a gas heater arranged to heat the sheath gas prior to entering the chamber.

Embodiments may also include one or more of the following. The collection medium is compatible with an aqueous fluid. The collection medium is compatible with a supercritical fluid. The collection medium is reflective at infrared wavelengths. The collection surface is transmissive at infrared wavelengths. The collection medium is a metal or semiconductor. The collection medium is a salt, e.g., KBr or Nacl.

Embodiments may also include one or more of the following. The system includes a liquid chromatograph for providing the flow of fluid. The liquid chromatograph is capable of operating at flow rates of about 150 µl/min or more. The liquid chromatograph is arranged for reverse phase operation by providing a fluid which includes an aqueous solvent. The system includes an infrared spectrometer. The collection medium is compatible with the infrared spectrometer to permit analysis of the components while on the medium. The system includes a mass spectrometer. The system includes a UV/VIS spectrometer. The system includes a thermal pyrolysis apparatus. The system includes a Raman spectrometer. The system includes a nuclear magnetic resonance spectrometer.

Embodiments of the invention can provide important advantages. For example, the systems can make deposition of components more practical and applicable to various applications because nozzle control is greatly improved, making small deposits from higher flow rates of nonvolatile solvents easier to attain. For example, the nozzle is capable of consistently operating at flow rates of around 200 µl/min or more, e.g., around 400 µl/min, with a reverse phase solvent, e.g., methanol/water (50%/50%) to deposit components in an area of about 1 mm or less. Accordingly, the sensitivity of spectroscopic analysis of the measurement is enhanced.

In addition to increased sensitivity, the long capillary nozzle can also provide increased spatial resolution of a deposited multi-analyte chromatogram. This allows one to use lower deposit surface translation rates, and more densely pack chromatograms onto deposit surfaces, thus facilitating automation of deposition and analysis.

Further, the effectiveness of the nozzles permits processing of components carried in fluids produced by various analytical methods and analysis by various spectroscopic and chemical analyses.

Further aspects, features, and advantages follow.

BRIEF DESCRIPTION OF THE DRAWING

FIG. 2 is a cross-sectional view of a nozzle assembly according to the invention, while FIG. 2A is a side view of the nozzle capillary in a linear configuration;

FIG. 3 is side view of a nozzle assembly according to the invention, while

STRUCTURE

Figure 1:
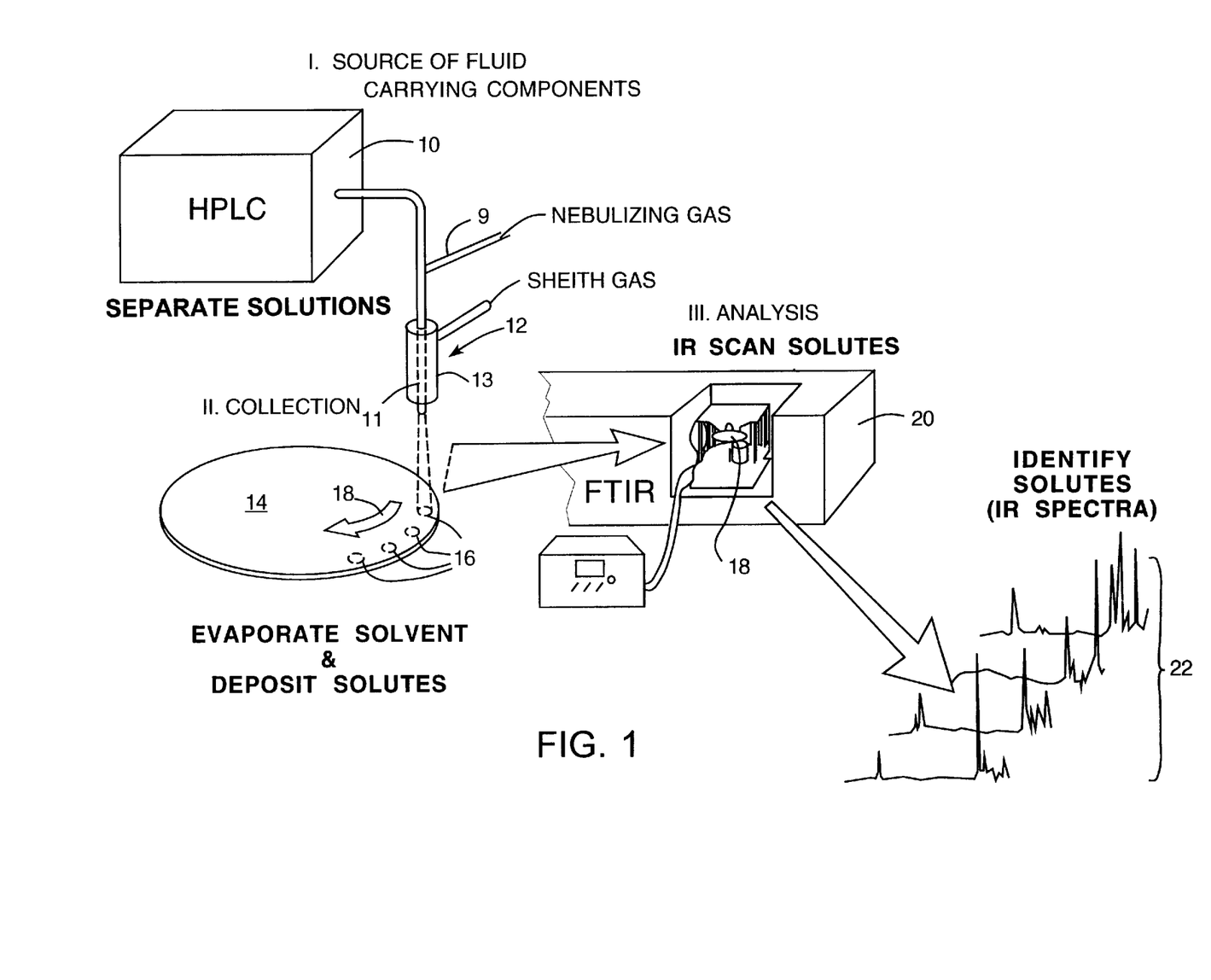
FIG. 1 is a schematic of the deposition and subsequent spectral analysis of components.

Referring to FIG. 1, an important application of the nozzle assembly described herein is collection of components that are separated on a chromatograph, such as a high performance liquid chromatograph 10. The effluent from the chromatograph 10 is directed to a nozzle assembly 12, which includes an inner, chromatographic effluent-directing tube 11 and an outer sheath gas-directing tube 13. A nebulizing gas 9 may optionally be mixed with the effluent upstream of the nozzle (not shown). The effluent is sprayed toward a collection surface 14 in a manner that the solvent is evaporated and the components are deposited in regions 16 along a path as the collection surface 14 is rotated (arrow 18). The collection surface 14 is a medium with properties that facilitate spectroscopic analysis, such as reflectivity, transmissivity, temperature and vacuum stability and is compatible with the chromatographic solvent and components.

After deposition, the collection surface is placed in an infrared spectrometer 20 and the deposits are analyzed to yield infrared spectra 22, which can be used to identify the chemical structure of the components. Systems of this general type are known in the art. Examples are provided in Biemann et al U.S. Pat. No. 4,823,009 and U.S. Pat. No. 4,823,243, the entire contents of which are incorporated herein by reference. A commercial system, the FT-Transform, is available from Lab Connections, Marlborough, Mass.

Figures 2, 2A:
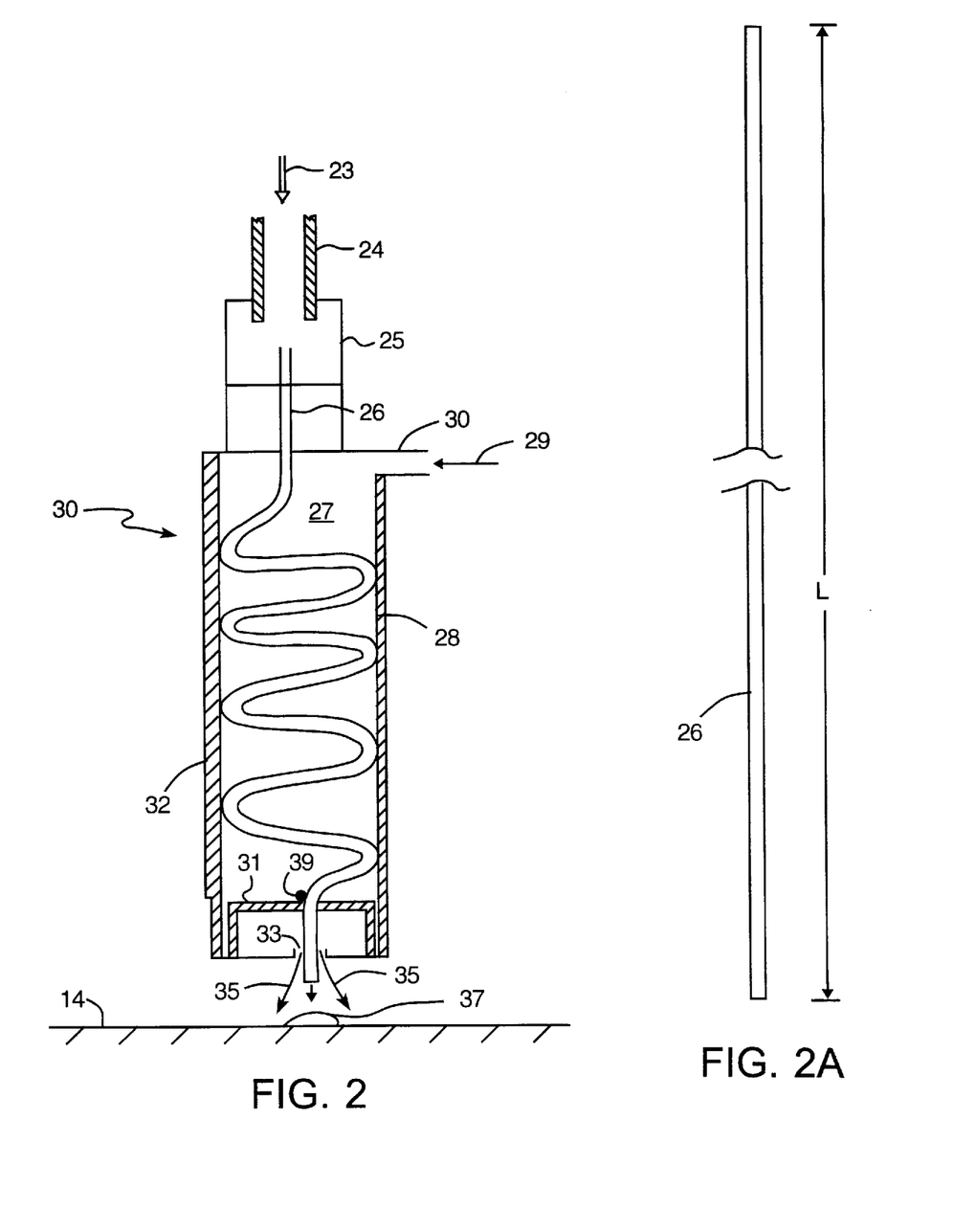

Referring to FIG. 2, in the systems of the invention, the effluent (with or without nebulizing gas) is directed (arrow 23) from chromatographic tubing 24 through a coupler 25 to a nozzle assembly 30 that includes a flexible, small diameter capillary 26 with an extended length, e.g., about 20 cm. For most of its length, the capillary is contained in a chamber 27 defined by a large diameter tubular chamber element 28 into which a sheath gas is directed (arrow 29) from a side arm 31. As illustrated, because of its extended length, the capillary may be wound within the chamber 27 to provide a nozzle assembly of convenient, practical dimensions for an analytical instrument. The length of the chamber may be, e.g., two-thirds, one-half, or even less than the length of the capillary. For example, the capillary can be coiled inside the chamber of a standard Swagelok® tube-fitting tee, which has a chamber length of about 5 cm.

The chamber also includes a centering collar 31 with an opening through which the capillary passes to center the capillary in an outlet opening 33 of the chamber element 22. The capillary may also include a bead 39 to control the extension through the opening 33. The system also includes a heater 32 extending along the length of the chamber which heats the sheath gas, which in turn heats the capillary along most of its length.

The capillary extends through opening 33 in the downstream end of the chamber element 28. The opening 33 has a diameter slightly larger than the outer diameter of the capillary to direct a flow of sheath gas (arrows 35) concentrically about and along the capillary toward a deposition surface 14. This creates a high velocity gas flow at the capillary tip and results in shear forces on emerging liquid which promotes small droplet size. The effluent emerges (arrow 37) from the lower tip of the capillary, is entrained in the sheath gas, and the non-volatile solutes are deposited on the collection surface 14 as small diameter spots 39 while the fluid is evaporated.

Referring as well to FIG. 2A, the capillary may have a length, L, of about 15–50, preferably 20–30 cm. The length of the capillary, as referred to herein, is the length measured when the capillary is in a substantially straight configuration, as illustrated. The inner diameter of the capillary is from 15 to 300, preferably 75 to 150 $\mu$m. The small diameter of the capillary is believed to increase the heat transfer surface/liquid volume ratio, thus facilitating heat transfer. The very thin walls of the capillary also facilitate this heat transfer.

Longer, smaller inner diameter capillaries can produce smaller diameter deposits, but also accommodate lower flow rates in practical applications. Viscous pressure drop is increased greatly with decreasing inner diameter (pressure drop will vary inversely to the fourth power of the diameter) and increasing length, requiring high pump pressures which may not be attainable with typical chromatographs. Higher pressures may also prevent the use of flow detectors upstream of the nozzle, or other equipment that has pressure limitations.

The capillary can be made of various materials such as fused silica (e.g., gas chromatography tubing), or preferably a metal such as stainless steel. For use in liquid chromatography interface applications, thin-walled stainless steel capillary is preferred over fused silica because of superior thermal conductivity and chemical imperviousness. Reverse-phase aqueous mobile phase solvents may dissolve silica in a fused silica capillary, and this may contribute to the component spectra. The capillary can be arranged in a nozzle assembly so that it is substantially straight, rather than coiled as shown in FIG. 2.

As illustrated in the Examples below, the long capillary nozzle designs permit a broad dynamic range of operation in terms of effluent flow rate and solvent volatility. It is believed that this is a consequence of uniform and gradual heat transfer to the fluid flowing within the capillary and uniform and very gradual pressure drop over the extended length of the capillary.

EXAMPLES

Example 1

Figure 3:
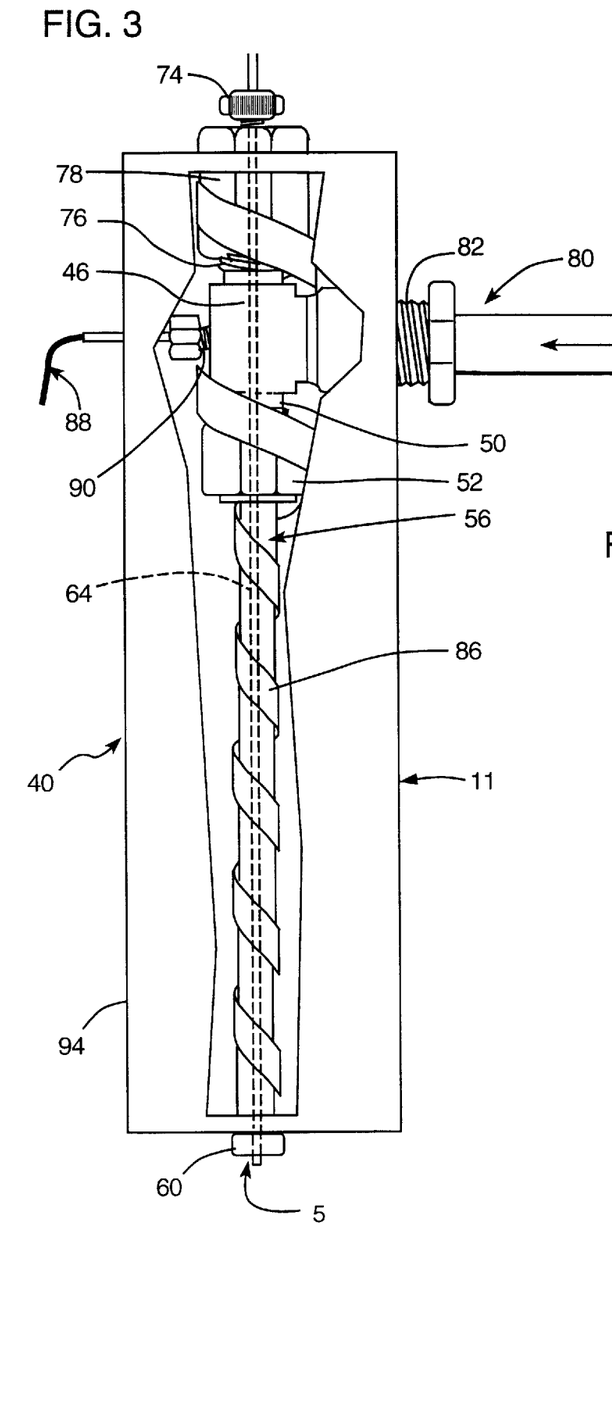

The following is an example a particular nozzle assembly. Referring to FIGS. 3 to 3D, the assembly 40 includes a chamber tube 56, a capillary 64, a gas heater 80, a tape heater 86, and a temperature sensor 88. The components are connected and assembled through a chromatographic coupler 46.

Figure 3A:
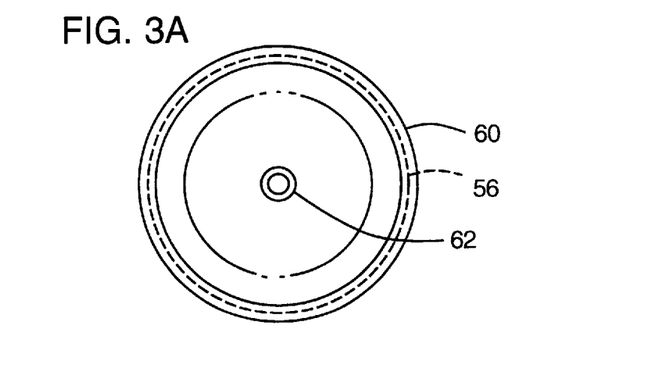
FIG. 3A is an end-on view.

Referring to FIGS. 3 and 3A, in a particular embodiment of a long capillary nozzle assembly 40, an outer sheath gas chamber tube 56 is connected to a lower arm of the four-way chromatographic coupler 46 (model TCEF411T, Valco Reactor Tee) through a nut and ferrule arrangement 52. The chamber tube 56 has an outer diameter of about ¼", an inner diameter of about 0.180", and is made of stainless steel.

Referring, as well, to FIG. 3A, the distal end of the tube 56 is provided with an orifice cap 60 which can be threaded to the tube 56. The orifice cap includes a central opening 62 through which capillary 64 extends, as will be discussed further below. The aperture has a diameter of about 0.025", which is larger than the capillary outer diameter (about 0.008 inch) to permit sheath gas to flow around the capillary and focus spray toward a collection medium. The sheath gas also provides shear to break liquid emerging from the capillary into small droplets. Aperture diameter is dictated by the sheath gas flow rate and the outer diameter of the capillary.

Figure 3B:
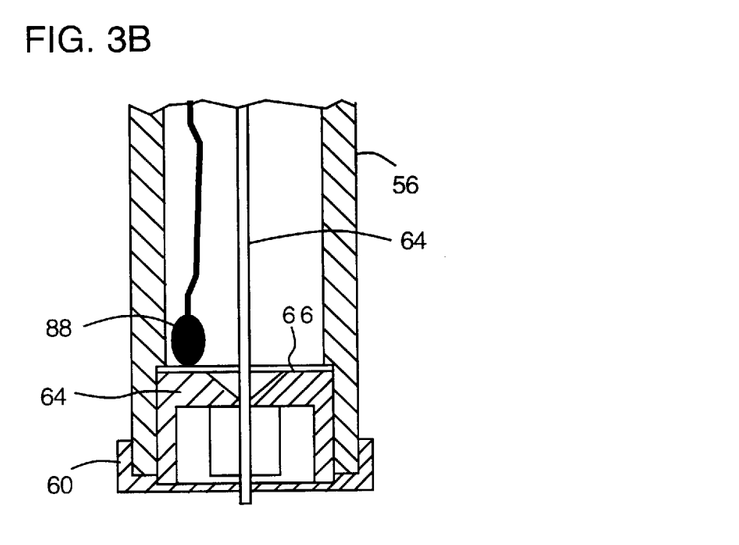
FIG. 3B is a cross-sectional view of an end portion.
Figure 3C:
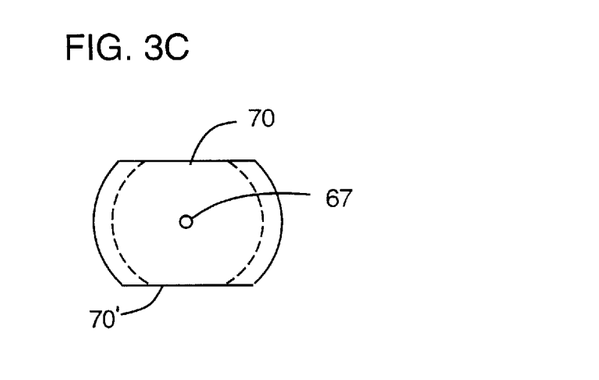
FIG. 3C is an end-on view of a component.
Figure 3D:
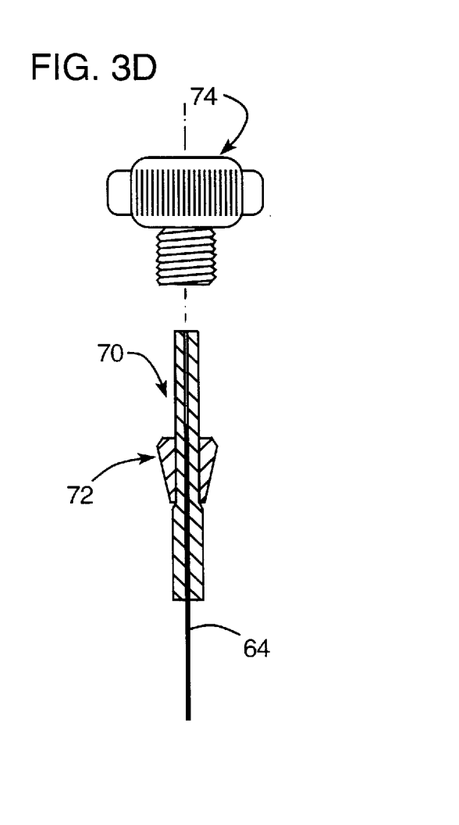
FIG. 3D is an exploded view of components of the nozzle in assembly FIG. 3.

Referring as well to FIGS. 3B and 3C, the cap 60 supports a centering collar 64. The centering collar 64 has an upper face 66 with a counter-sunk aperture 67 with a through hole slightly larger than the capillary 64. The collar 64 is cut from cylindrical form to create sides 70, 70' which allow passage of sheath gas between the collar and the inner wall of tube 56. Different centering collars may be utilized to provide a close fit to different diameter capillaries. The collar also prevents the capillary from touching the sides of the opening 62.

The flexible capillary 64, has a length of about 20 cm and an inner diameter of about 100 $\mu$m (stainless steel, available from Micro Group, Inc, Medway, Mass). The capillary has an outer diameter of about 0.008". The tip of the capillary is square (form a face normal to the capillary axis) and beveled (in the manner or a circular punch or cork borer). The capillary is cut by heating a section of stainless steel tubing in a flame or by locally applying electric heating, then pulling it to snap the capillary apart. When using electric heating, electrode leads are clamped to the capillary where it is to be "cut". The electrodes are attached to low voltage power supply; and voltage is increased until the capillary glows a dull cherry red. The capillary is then pulled. This results in a clean square fracture. The capillary is beveled by electropolishing. The capillary assembly is connected to the anode and the top of the tube is immersed in electrolyte (cathode). The tube is carefully pulled up to form a liquid meniscus at the very tip of the tube. When voltage is applied, the result is a uniform tapered bevel. Other conventional small scale metal cutting techniques that produce a clean, smooth, square or beveled cut are also acceptable.

Referring as well to FIG. 3D, the capillary 64 is passed through a short length, e.g., about 3 cm, of ¹⁄₁₆" outer diameter, 0.008–0.009" inner diameter, high pressure polymeric chromatography tubing 70. A polymeric chromatography ferrule 72 is placed over the tubing 70. The inner diameter of the chromatography tubing is slightly larger than the outer diameter of the capillary and can be swaged to the capillary by a nut 74 which compresses the ferrule 72.

The capillary is inserted through an arm 76 of the four-way chromatographic coupler 46. The arm 76 includes a nut 78 which is sized to receive the tubing section 70. The nut 78 also receives the nut 74. The ferrule 72 is crimped by tightening the nut 74 into the nut 78, to deform the chromatography tubing and firmly grip the capillary. The capillary is adjusted for correct protrusion length (about 0.5–2 mm) at the bottom of the nozzle. Protrusion length is controlled by placing a slight bend in the capillary, just above the centering collar, or by welding a bead of metal onto the capillary at this point (so that the capillary cannot protrude too far). (A helical coil will provide some spring force to push the capillary down until the bend/bead at the top of the centering collar restrains excessive protrusion.) This assembly is then inserted into the nozzle body, and checked for protrusion length at the orifice cap. If necessary the capillary length is adjusted. The nut 58 is then tightened to secure the capillary.

The assembly also includes two heat sources. One is an electric gas heater 80 (model AH37-4MF available from Hotwatt). The gas heater is connected to the coupler 46 at a side arm 82. Sheath gas flows through the heater prior to entering the coupler, where it is directed into the chamber tube 56 and around the capillary 64. The second heater is electrical heating tape 86 which is wrapped around the outside of the chamber tube 56. The second heater may also be provided by, e.g., machining the nozzle body from a block of (thermally conductive) material; which is heated by strap heaters, rod heaters, etc. Both of the heat sources are controlled by an industrial temperature controller (model CAL 3200, available from CAL Controls).

A temperature sensor 88, such as a thermocouple, resistance sensor, or thermistor is threaded through an arm 90 of the coupler 46 and located near the collar 56 inside the chamber 56. The assembled nozzle is contained within an insulating jacket 94 made of e.g., stainless steel.

A nebulizer gas is provided upstream of the nozzle assembly (not shown). When nebulizer gas is used, it is continuously injected into the liquid flow upstream of the nozzle at flow rates of 10–14 cc/min. The admixing of nebulizer gas into the liquid flow stream has the effect of breaking the liquid flow into a series of packets. The result is an increased nozzle capacity, typically on the order of 10%–40%. If a nozzle is delivering a desired spray pattern at a given set of flow and sheath gas conditions, the use of a nebulizer gas will permit an increase in solvent flow rate. The application of a second gas flow stream is described in Biemann U.S, Pat. No. 4,823,009, incorporated supra.

In use, sheath gas flow rate is typically about 4–8, preferably 4–6 cpm. In most applications, the flow rate of sheath gas can be altered considerably within this nominal range without marked change in nozzle performance. The choice of sheath gas composition is not critical. It can be nitrogen, helium, clean and dry air, or any other appropriate gas. Helium, having high thermal and diffusive coefficients, is preferable; but does not confer a major advantage over less expensive gases.

The nozzle is controlled by fixing the sheath gas flow rate, and adjusting the sheath gas heater input to achieve a desired temperature at the nozzle tip. Sheath tip temperature is maintained within +/−3° C. of the optimum setting. Higher temperature results in solvent flash within the capillary, solute precipitation, and plugging of the capillary. Lower temperature results in too wet a deposit, and the deposit is washed out into two parallel tracks ("washout").

The nozzle tip is positioned about 3–10 mm above the surface of the collection medium. For a given chromatography solvent system there is an optimum height. Putting the nozzle too close to the deposition surface causes the deposited solutes to "blow out". As the nozzle is raised above the optimum height the diameter of the deposit increases. Inasmuch as the pattern widens gradually with increased nozzle height, this is not a highly critical setting. To maximize sample density, the nozzle can optionally be angled a few degrees off vertical, in a plane normal to the horizontal translation axis of the collection surface. When large quantities of solutes are deposited, the deposit radius increases. By angling the nozzle normal to the translation path of the collection surface, the excess solutes deposit off the translation axis, and higher spatial resolution of a series of rapidly changing solutes can be maintained (at the expense of quantitative information regarding higher quantity solutes, a large part of the deposit would be off the scan axis of the infrared optics). Modern spectrometers incorporate microscope optics that permit the focusing of the incoming energy optical beam to a spot of several microns diameter. Maximum spectrometric sensitivity is achieved when a sample is concentrated into an area somewhat larger than the optical beam dimensions. Spectral aberrations can arise if the sample dimensions are smaller than the beam dimensions, or if the sample has a non-uniform thickness within the area of the optical beam. As a practical consideration then, the deposited spot should be enough larger than the beam to present a uniform thickness of sample within the beam scan region.

Figure 4A:
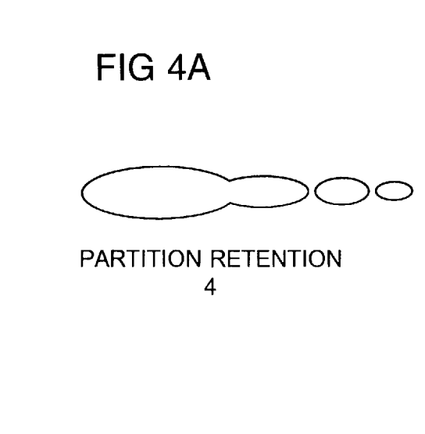
FIGS. 4A–4D illustrate the shape of deposits from nozzles under varying conditions.
Figure 4B:
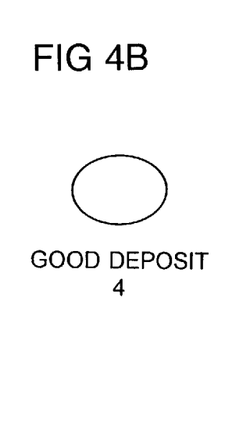
Figure 4C:
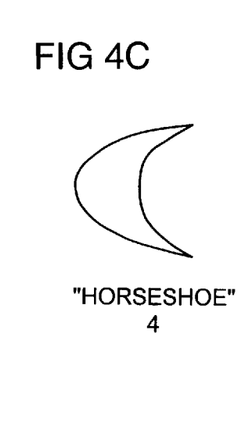
Figure 4D:
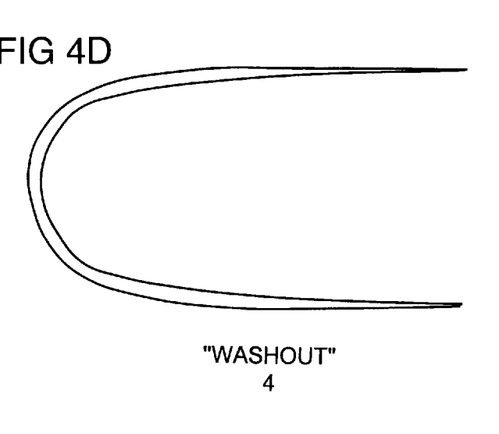

Referring to FIGS. 4A–4D, the effects of the match and mismatch of solvent flow rate and nozzle operating conditions on component deposition are illustrated. In this illustration nozzle gas flow and temperature conditions are held constant while the liquid flow is varied. Referring to FIG. 4A, insufficient liquid flow, premature solvent vaporization occurs within the capillary, and solute material is partially retained within the capillary. Gradually the solute is released. The net effect is a tail of solute release after a bolus injection. Referring to FIG. 4B a solute deposition is illustrated when the solvent flow rate is properly matched to the nozzle gas flow and temperature. An injected solute bolus appears as a uniform compact deposit. Referring to FIGS. 4C and 4D the effect of excessive solvent flow are demonstrated. In this situation, the solvent flow exceeds the evaporative capacity of the nozzle, resulting in a wet spray. This residual solvent has the effect of re-dissolving deposited solutes, and washing them out radially from the focus of the nozzle spray jet.

In this embodiment, the nozzle will exhibit over 100 psi inlet pressure at 0.2 ml/min solvent flow rate (solvent: 50:50 water/methanol).

Example 2

A set of experiments was performed with four nozzles with designs outlined in Table I. The nozzles utilized capillaries of differing dimensions. The "Standard" nozzle is manufactured and sold on the LC-Transform instruments manufactured by Lab Connections, Inc. As the table indicates, it has a short capillary length, about 7.1 cm, and a relatively large capillary inner diameter, about 300 μm.

The Restrictor Tip nozzle is a "Standard" nozzle, modified by brazing a capillary with a short length, about 1 cm and relatively small diameter, about 100 μm into the delivery tip of the 300 μm capillary. The "short capillary nozzle" has a short capillary length, about 7.1 cm and a smaller inner diameter, about 100 μm. The long capillary nozzle is the nozzle described in Example 1, having a length of 20 cm and an inner diameter of about 100 μm.

The component deposits were examined for size and character (see FIGS. 4–4C). The standard nozzle had a maximum flow capacity for acceptable component deposition of 40 μl/min and delivered a component spot of 2.5 mm diameter. For the experimental nozzles, results obtained at various solvent flow rates are summarized in Table III.

TABLE III

NOZZLE PERFORMANCE

| SOLVENT FLOW | SHORT CAPILLARY NOZZLE | | RESTRICTOR TIP NOZZLE | | LONG CAPILLARY NOZZLE | |
|---|---|---|---|---|---|---|
| | DEPOSIT DIAM., mm | COMMENTS | DEPOSIT DIAM., mm | COMMENTS | DEPOSIT DIAM., mm | COMMENTS |
| 20 μl/min | 1.2 | compact | 1.5 | compact | 0.4 | compact |
| 50 μl/min | 1.5 | bow | 1.6 | bow | 0.5 | compact |
| 70 μl/min | | washout | 2.8 | bow | 0.6 | compact |
| 150 μl/min | | washout | | washout | 0.7 | compact |

TABLE I

NOZZLE DESIGNS

| NOZZLE TYPE | CAPILLARY INNER DIAMETER | CAPILLARY LENGTH |
|---|---|---|
| "Standard" LC-Transform nozzle | 300 μm | 7.1 cm |
| Restrictor Tip nozzle | 100 μm | 1 cm |
| Short Capillary nozzle | 100 μm | 7.1 cm |
| Long Capillary nozzle | 100 μm | 20 cm |

Deposits were made using each of the four nozzles at varying solvent flow rates. The nozzles were evaluated using an HPLC pump for solvent delivery and a manual injector valve for delivery of solutes into the solvent stream. No chromatography column was used. All depositions were conducted with the collection surface at room temperature and at atmospheric pressure. The deposition conditions are set forth in Table II.

TABLE II

EXPERIMENTAL CONDITIONS

| | |
|---|---|
| Solvent | 50/50 (v/v) MeOH/H₂O |
| Solute | Rhodamine B: 0.05% in 50/50 MeOH/H₂O |
| Solute Injection Volume | 2 μl |
| Nebulizer Gas Flow | 20 cc/min |
| Sheath Gas Flow | 5 liters/min |
| Nozzle Height (above deposition surface) | 4 mm |
| Deposition Surface Translation Rate | 2.5 mm/min |
| Solvent Flow Rates | (see Table III) |

For each experimental condition, the sheath gas temperature was adjusted to yield optimum deposition pattern of the solute. Achievable temperature of sheath gas for these experiments was 130° C. when using the restrictor tip and short capillary nozzles, which did not have a second heater, i.e., heating tape. The long capillary nozzle which included a heating tape second heater could achieve sheath gas temperatures of 155° C. It is believed that higher temperatures would not have improved the results for the restrictor tip or short capillary nozzle.

As the results illustrate, the long capillary design provides both a higher evaporative capacity and a smaller deposit spot size. Attempting to increase solvent flow in a short capillary nozzle leads to insufficient evaporation of solvent, with consequent washout of deposited solutes. Attempts to compensate by increasing the temperature of the sheath gas caused the nozzle to enter an unstable regime in which solvent vaporizes in the capillary, and the solute precipitates erecting a solid plug which results in cessation of flow.

The long capillary design provides a higher attainable sensitivity in the spectral analysis of deposits. The 20 cm capillary nozzle can yield a sensitivity increase of ca 25×over the 7 cm capillary nozzle, due to capacity and deposit diameter. Practical comparisons of sensitivity were made by taking infrared spectra of deposits from each of the four nozzles of organic compounds. The standard nozzle, (2.5 mm deposit diameter), yields a practical lower limit of about 1 microgram. Below this amount, noise and background aberrations degrade spectral quality. The 100 μm I.D. long capillary nozzle (0.4 mm deposit) used in conjunction with an infrared spectrophotometer equipped with microscope optics will provide good spectra at the 10–20 nanogram level.

Example 5

In this example, the mobile phase tetrahydrofuran (THF), a frequently used mobile phase, especially for GPC, was used. The solute was 0.05% Gentisic acid in THF.

TABLE IV

NOZZLE DESIGN/CONDITIONS

| | |
|---|---|
| Capillary inner diameter: | 100 μm/20 cm |
| Injection volume: | 2 μl |
| Sheath gas: | 5 lpm |
| Nozzle height: | 4 mm |
| Germanium collection surface traverse rate: | 5 mm/min |

The results for different flow rates are given in Table V.

TABLE V

| Solvent Flow Rate | Nozzle Temperature | Deposit |
|---|---|---|
| 0.3 ml/min | 123° C. | 1.0 mm |
| 0.4 ml/min | 142° C. | 1.0 mm |
| 0.7 ml/min | 195° C. | 1.0–1.1 mm |

Deposits are well formed, with no bowing or washout. For comparison, the standard nozzle we use on the LC-Transform can process 100–125 μl/min of THF, and deposit widths typically are 2.3–3.5 mm.

Other Embodiments and Uses

Use of capillaries of still smaller diameter will provide corresponding reductions in deposit diameters. As an example, the substitution of a 50 μm I.D. capillary in the long capillary nozzle will produce deposits with a diameter of 0.2 mm. Offsetting this improvement is a reduced solvent processing capacity, higher operating pressure, and a tendency to plug more readily. Increased capillary length will also provide increased solvent processing capacity in accordance with the art taught here. In practice, capillaries are selected to optimize performance for the analytical method applied to the deposit.

The nozzle has applications in a variety of interface methods. The Examples cited show how the nozzle is used to interface reverse phase or GPC liquid chromatography and infrared spectroscopy. The nozzle can also be used to collect sample components from other liquid chromatography techniques such a normal phase, size exclusion, and ion chromatography and separation methods such as flow injection analysis (FIA), Field Flow Fractionation, and Temperature Rising Elution Fractionation. The collected deposits from the nozzle can also be analyzed by a variety of methods, including Raman and micro Raman Spectroscopy, Thermal Pyrolysis, UV/Visible Transmission and Reflectance Spectroscopy, Nuclear Magnetic Resonance, and Mass Spectroscopy, including secondary ion mass spectroscopy (SIMS) and laser ionization mass analysis (LIMA), and other techniques such as thermal-gravimetric analysis, Auger, x-ray photoelection spectroscopy (XPS or ESCA), visible and electron microscopy and, other techniques, particularly those that are suitable for examination of thin films, surfaces, and deposits. The deposits may be analyzed on the deposition medium, as described in the Examples, or the deposits may be removed from the medium and transferred to another suitable sample holder for analysis. The nozzles may also be provided in coupled systems in which the deposition surface is within the spectrometer or other analytical instrument while deposition takes place.

Further embodiments are within the following claims.

What is claimed is:

1. A system for processing fluid carrying a component by depositing the component onto a medium and evaporating the fluid, comprising:

a collection medium, and a nozzle arrangement including a capillary with a first, inlet end for receiving flow of said fluid carrying said component and a second, outlet end, a heater for heating a substantial region of the capillary, and a sheath gas directed toward said collection medium in a manner that said fluid is exposed to said sheath gas after emerging from said outlet end of said capillary, wherein said capillary has an inner diameter of about 15 to 300 μm and a length of about 20 cm or more.

2. The system of claim 1 wherein said capillary has a length of about 15 to 50 cm.

3. The system of claim 1 wherein said capillary has a length of about 20 to 30 cm.

4. The system of any one of claims 1 to 3 wherein said capillary has an inner diameter of about 75 to 200 μm.

5. The system of any of claims 1 to 3 wherein said capillary has an inner diameter of about 100 μm.

6. The system of claim 1 wherein said capillary is arranged in a bent configuration such that the inlet end and outlet end are positioned at a distance less than said length.

7. The system of claim 6 wherein said capillary is bent in helical fashion.

8. The system of claim 6 wherein said distance between said inlet end and said outlet end is about 5 cm or less.

9. The system of claim 6 wherein said capillary is substantially contained in a chamber having dimensions less than the length of said capillary.

10. The system of claim 9 wherein said chamber is arranged to receive said sheath gas and direct said sheath gas toward said collection medium.

11. The system of claim 10 wherein said chamber includes a heater.

12. The system of claim 11 wherein said heater is arranged to heat said chamber.

13. The system of claim 12 further comprising a gas heater arranged to heat said sheath gas prior to entering said chamber.

14. A system for processing a fluid carrying a component by depositing the component onto a surface and evaporating the fluid, comprising:

a collection mendium, and a nozzle arrangement including a capillary with a first, inlet end for receiving a flow of said fluid carrying said component and a second, outlet end, a heater for heating a substantial region of the capillary, and a sheath gas directed toward said collection surface in a manner that said fluid is exposed to said sheath gas after emerging from said outlet end of said capillary, wherein said capillary has an inner diameter of about 15 to 300 μm and a length of about 20 cm or more and is arranged in a bent configuration such that the inlet end and outlet end are positioned at a distance less than said length, said capillary being substantially contained in a chamber arranged to receive said sheath gas and direct said sheath gas toward the collection medium and said chamber includes a heater.

15. The system of claim 14 wherein said capillary is bent in a helical fashion.

16. The system of claim 14 wherein said capillary has a length of about 20 to 30 cm and an inner diameter of about 75 to 200 μm.

17. A system for processing chromatographic effluent fluid carrying a component to facilitate spectroscopic analysis of the component by depositing the component onto a medium and evaporating the fluid, comprising:

a collection medium compatible with said fluid and suitable for use in spectroscopic analysis, and a nozzle arrangement including a capillary with a first, inlet end for receiving a flow of said fluid and a second, outlet end, said capillary having a length of about 20 to 30 cm and an inner diameter of about 75 to 150 μm and being arranged in a bent configuration such that the inlet end and the outlet end of said capillary are positioned at a distance that is less than the length, a chamber for substantially containing said capillary, wherein said chamber is arranged to receive a sheath gas and to direct said sheath gas toward said collection medium such that said fluid is exposed to said sheath gas after emerging from said outlet end of said capillary and a heater for heating the capillary over a substantial region upstream of the outlet end.

* * * * *